United States Patent [19]
Eland et al.

[11] Patent Number: 5,171,230
[45] Date of Patent: Dec. 15, 1992

[54] FAST FLUSH CATHETER VALVE

[75] Inventors: Michael Eland, Dublin; Charles R. Patzer, Columbus; Jon F. Short, London, all of Ohio

[73] Assignee: Medex, Inc., Dublin, Ohio

[21] Appl. No.: 800,126

[22] Filed: Nov. 29, 1991

[51] Int. Cl.5 .............................................. A61M 5/00
[52] U.S. Cl. ..................................... 604/250; 604/246
[58] Field of Search ............... 604/250, 256, 237, 246, 604/247, 248, 249; 128/685, 673

[56] References Cited

U.S. PATENT DOCUMENTS

| | | | |
|---|---|---|---|
| 2,934,314 | 4/1960 | Chambers et al. ................... | 251/331 |
| 4,624,662 | 11/1986 | Le . | |
| 4,648,868 | 3/1987 | Hardwick et al. . | |
| 4,696,305 | 9/1987 | von Berg . | |
| 4,739,770 | 4/1988 | Stephens et al. ..................... | 604/246 |
| 4,934,375 | 6/1990 | Cole et al. . | |
| 4,960,259 | 10/1990 | Sunnanvader et al. .............. | 604/250 |

FOREIGN PATENT DOCUMENTS 2207736  2/1989  United Kingdom ................ 604/246

Primary Examiner—C. Fred Rosenbaum
Assistant Examiner—Manuel Mendez
Attorney, Agent, or Firm—Wood, Herron & Evans

[57] ABSTRACT

A fast flush catheter valve is disclosed having a valve body with a longitudinal bore therethrough for the flow of fluids through the valve. A tube is mounted substantially transverse to the longitudinal bore to substantially block the longitudinal bore. An actuating member is mounted through the exterior of the valve body so that one end of the actuating member is proximate the tube and the second end extends beyond the exterior of the valve body. A resilient biasing flange connects the second end of the actuating member to the exterior of the valve body. A capillary is mounted through the tube to provide a drip rate flow. Depressing the second end of the actuating member deforms the tube to produce a flush rate around the tube and releasing the second end causes the resilient flange to return the actuating member to a position where the tube can elastically return to the longitudinal bore blocking position. The valve is constructed from a few components and is simply and inexpensively constructed.

10 Claims, 3 Drawing Sheets

FAST FLUSH CATHETER VALVE

FIELD OF THE INVENTION

This invention relates generally to valves used in medical applications, and more particularly, to valves having both drip and flush flow rates.

BACKGROUND OF THE INVENTION

Fast flush valves are used in catheter systems in which the blood pressure of a patient is monitored. A typical catheter system includes a saline solution source that is connected by tubing to an inlet of a fast flush valve and an outlet of the valve is connected to a pressure transducer. Downstream of the pressure transducer, a three way stopcock is typically connected by tubing between the pressure transducer and a catheter that is inserted in the patient. This catheter system permits the flow of saline solution from the source through the valve, transducer, and stopcock to the catheter and then the patient.

A capillary mounted within the fast flush valve reduces the saline solution flow to a drip rate that prevents the blood of the patient at the catheter insertion site from clotting. Thus, the saline solution in the tubing connecting the pressure transducer to the catheter remains in fluid communication with the blood of the patient. The fluid communication between the saline solution at the pressure transducer with the blood of the patient permits the blood pressure of the patient to be monitored. When a larger volume of saline solution is needed to purge impurities from the system, the valve is actuated to provide a flush flow through the valve which clears the system out.

While the use of fast flush valves within such catheter systems is previously known, these valves have been relatively expensive to produce. Typically these valves require a number of components that require alignment and careful assembly to produce a reliable and fluid tight valve. The manufacturing process of such a valve can be either labor intensive or require intricate machinery to perform the assembling tasks. What is needed is a fast flush valve for use in a catheter system that is simple to construct and inexpensive to make.

SUMMARY OF THE INVENTION

It is an object of the present invention to provide a fast flush valve that can be used in a catheter system that is simple to manufacture and inexpensive to make.

The object of the present invention is achieved in a flush valve easily constructed from a few simple components. The valve of the preferred embodiment of the invention includes a valve body having a longitudinal bore through the body for fluid flow. An elastomeric tube is mounted through the valve body and transversely to the bore to normally block the flow of fluid through the longitudinal bore. A capillary is inserted through the tube so that it is aligned with the longitudinal bore and transverse to the tube. The capillary provides a drip flow rate through the valve when the tube is in the normally fluid blocking position. An actuator is mounted on the valve body and has an end that is proximate the tube. The other end of the actuator extends from the valve body and terminates in a button surface. The button may be depressed to cause the other end of the actuator to deform the tube and thereby open the longitudinal bore to permit a flush flow through the bore of the valve. The actuator further includes a pair of hinged wings that have plugs mounted along a surface of each wing. The wings are pivoted towards the valve body so the plugs may be inserted into the ends of the tube to secure the actuator to the valve body and to urge the tube outwardly into fluid tight engagement with the longitudinal bore.

The valve of the present invention is simple to assemble. The valve body is formed with the longitudinal bore, actuator bore, and valve core bore at right angles to each other. The tube is press fitted into the valve core bore and an O-ring seal is inserted in a well surrounding the actuator bore. The O-ring seal is secured in the well by a snap-fit cap 10 and the actuator is placed in the actuator bore. A radial diaphragm extends from one end of the actuator to a collar which rests on the valve body. Two wings pivotably joined to the collar are rotated towards the valve to insert a plug extending from each wing into each end of the tubular valve core. Integral hooks formed on the outboard end of the wings engage grooves in the valve body to hold the wings and plugs in place.

One advantage of the present invention is a valve having relatively few components with relatively simple geometries.

Another advantage of the present invention is the use of relatively inexpensive materials to form the components of the valve.

The structure, operation and advantages of the presently preferred embodiment of this invention will become further apparent upon consideration of the following description taken in conjunction with the accompanying drawings.

DETAILED DESCRIPTION OF THE INVENTION

Figure 1:
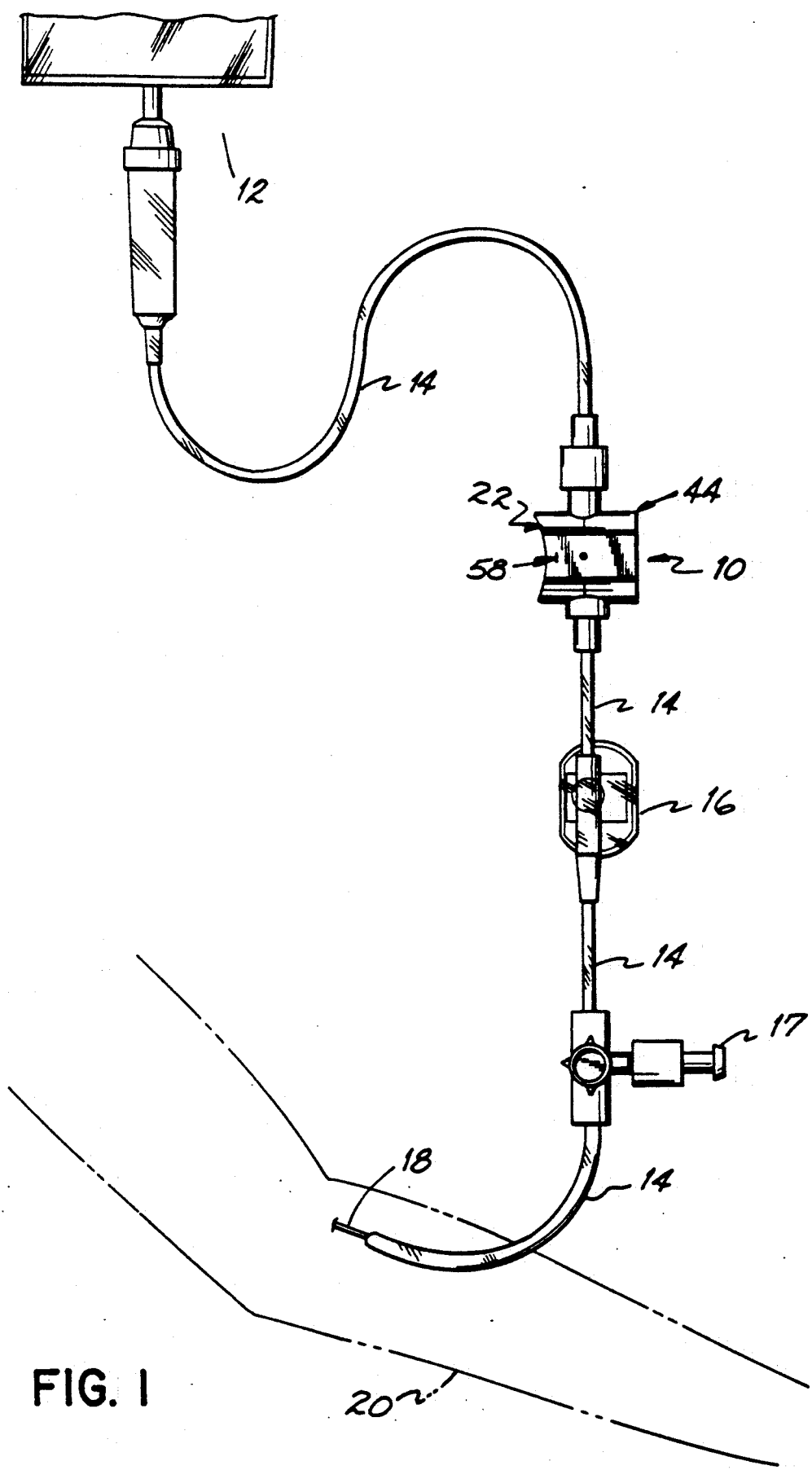
FIG. 1 is a perspective of a fast flush valve constructed in accordance with the principles of the present invention.

FIG. 1 shows a fast flush valve 10 constructed in accordance with the principles of the present invention in its most typical use. A fluid source 12 such as a saline bottle or bag is connected via tubing 14 to flush valve 10. Tubing 14 leads from valve 10 to a pressure transducer 16 which is used to measure the patient's blood pressure. Downstream of the transducer 16 is a stopcock 17 that may be used to withdraw blood samples or infuse medicines or contrast agents into the patient. Tubing 14 leads from the stopcock 17 to a catheter 18 that is inserted into the arm 20 of a patient.

In the use depicted in FIG. 1, valve 10 performs two functions. The first is to permit a relatively high volume flow rate of fluid to clear air from the tubing and needle downstream of the valve prior to insertion into the patient's arm or to clear blood from the line to prevent clotting after a blood sample withdrawal through the stopcock. The second is the provision of a steady drip rate of the fluid from source 12 through valve 10 to keep blood from clotting at the needle in the patient's arm.

Figure 2:
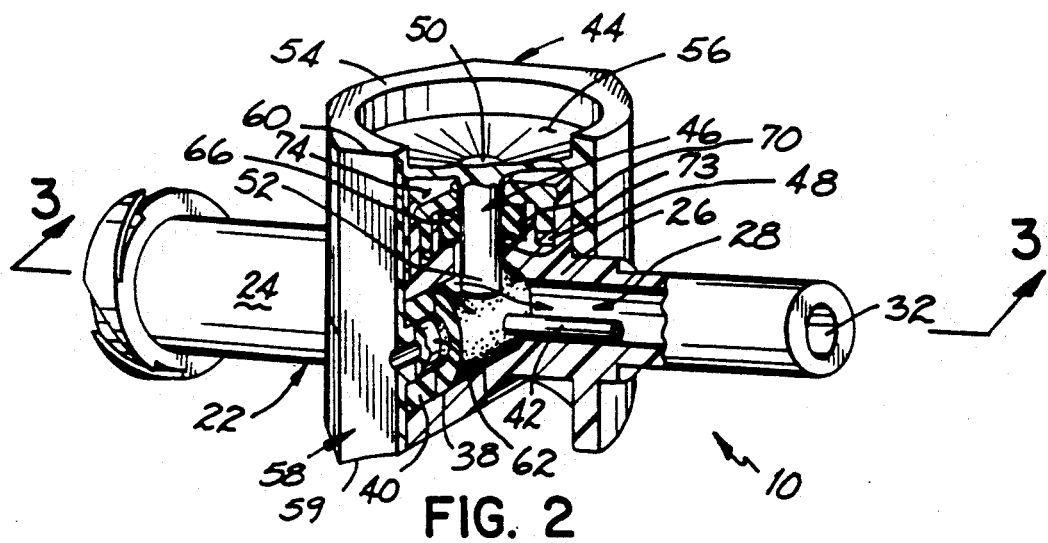
FIG. 2 is a cut-away view of the valve shown in FIG. 1.

The construction of the fast flush valve 10 is shown in more detail in FIG. 2. The valve 10 has a valve body 22 having an exterior surface 24 and an interior 26. A longitudinal bore 28 connects an inlet 30 through the interior 26 of the valve body 22 to an outlet 32. Transversely oriented with respect to the bore 28 is a valve core bore 38 (best shown in FIG. 5). Press fitted within the valve core bore is an elastic tube 40 which blocks bore 28 from the outlet 32. A capillary 42 extends through valve core 40 to provide a drip flow of fluid through the longitudinal bore 28 of valve 10.

Valve core tube 40 is preferably formed from a resilient, deformable material with an elastic memory. In the preferred embodiment of the present invention, core 40 is formed from Silastic TM tubes manufactured by Dow Corning Plastic Co. of Hemlock, Mich. and preferably has a rating of 35-50 on the Durometer scale. Alternatively, the valve core may be made of latex or silicone having the same Durometer rating.

Capillary 42 is formed from deformable tubing such as PEEK TM tubing manufactured by The Munhill Company of Worthington, Ohio so that it is not destroyed by the deforming of the valve core 40. The capillary is preferably a standard size tube with a 0.0025 inch inner diameter with a tolerance of ±0.0005 inch. Capillary 42 preferably provides a drip flow rate of a nominal 3 cc per hour for an adult care system and 30 cc for a neonatal care system as is well known within the art.

Also shown in FIG. 2 is a pushbutton actuator 44 that is mounted to the top of the valve body. The actuator 44 includes a central actuating member 46 slidingly received in a vertical actuator member bore 48 in the body 22. The actuating member 46 has an upper end 50 and a lower end 52. Radially extending from the upper end 50 to a collar 54 is a biasing diaphragm 56. The collar 54 rests on a ridge 55 on the body and has two diametrically opposed mounting wings 58 that are hinged to the collar 54 at joint 60 (best shown in FIG. 5). A plug 62 extends from each of the wings 58 and the plug is pressed into the ends of the tube 40 to further expand the tube 40 into a fluid tight engagement with bore 38 and to secure actuator 44 to the valve body 22.

Figure 5:
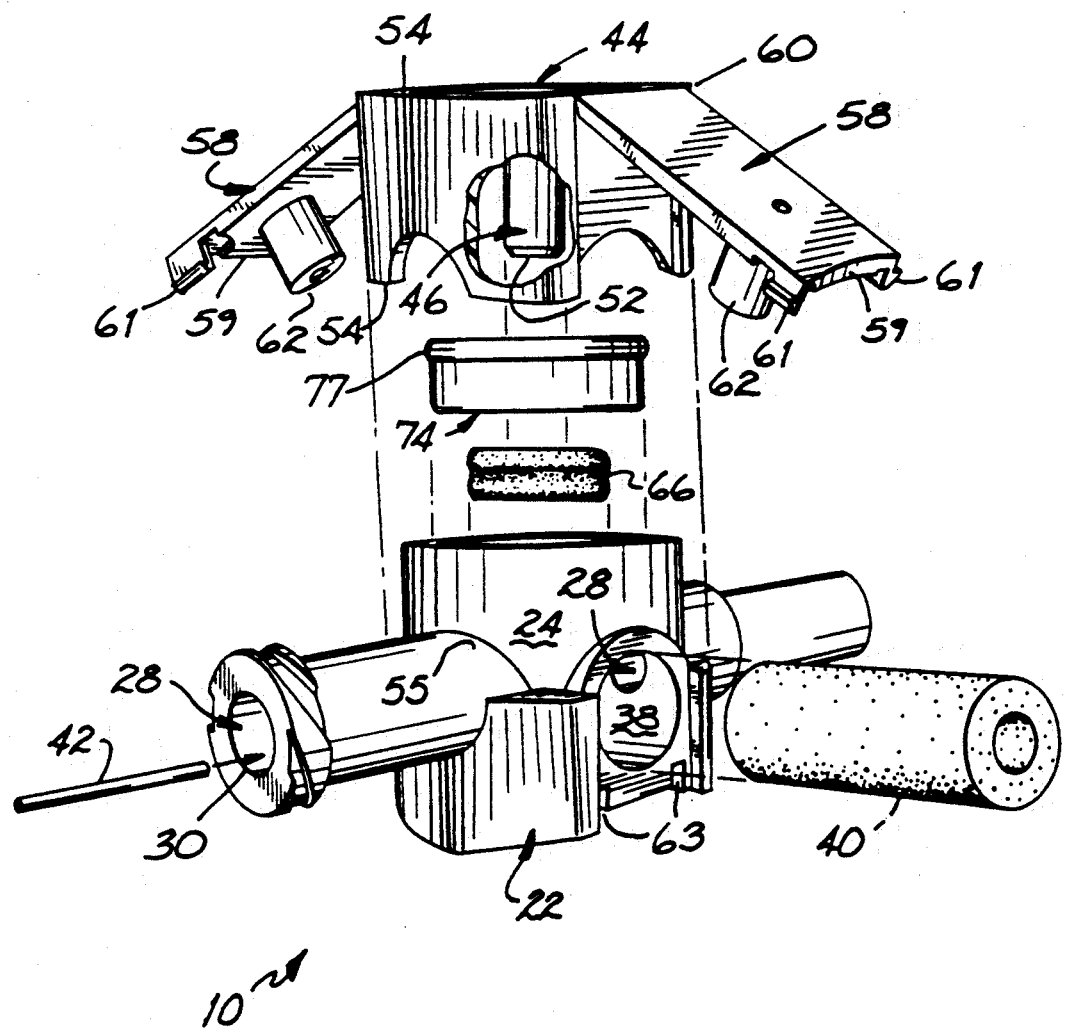
FIG. 5 is an exploded view of the valve showing the assembly of the components to form the valve.

At the outboard ends 59 of wings 58, shown in FIG. 5, are integrally formed hooks 61 that seat within grooves 63 which are located on the valve body 22 below valve core bore 38. The securement of the hooks 61 within the grooves 63 helps prevent the plugs 62 from being pushed out of the valve core 40. The tight fit of the actuator 44 to valve body 22 helps ensure the liquid tightness of the valve 10.

The actuator 44 is made of a resilient material with elastic memory. This provides radial diaphragm 56 with sufficient flex to return actuator member 46 to the position in FIG. 3 when actuating member 46 is released from a vertically displaced position. Valve body 22 is preferably formed from molded plastic with bore 28, valve core bore 38, and actuator member bore 48 formed therein, preferably at right angles to one another.

Figure 3:
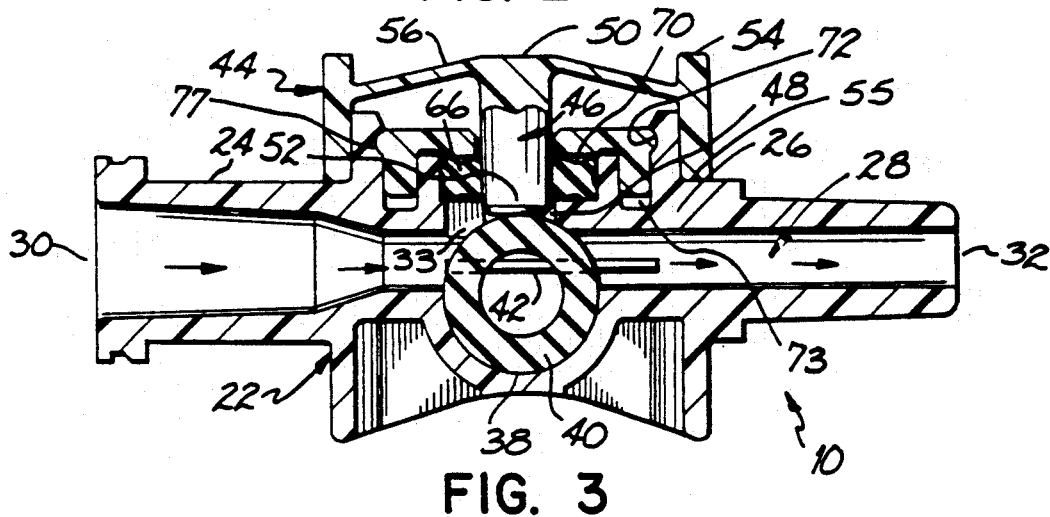
FIG. 3 is a cross-sectional view of the valve in FIG. 2 taken along lines 3—3.

As shown in FIG. 3, O-ring seal 66 is concentrically mounted about the actuating member 46 within seal cavity 70 to prevent fluids within longitudinal bore 28 from rising upwardly through vertical bore 48. Snap fitted into a circular groove 72 along the circumference of a well 73 in the valve body 22 is a rounded flange 77 formed along the circumference of a cap 74. The fit of the flange 77 within the groove 72 further ensures the fluid integrity of the valve 10 and the secure attachment of the actuator 44 to the valve body 22.

A relief area 33, FIG. 3, is provided in bore 28 on the inlet side of valve core 40. This relief area provides an area for back flow through the valve if an attendant injects material into the tubing 14 through stopcock 17 with the stopcock in a position which directs the material upstream. The pressure created from the injection may be sufficient to damage the pressure transducer 16 if the material is not allowed to pass back through the bore 28. Because the valve 10 permits this back flow, the transducer is not damaged and the attendant can correct the error by turning the stopcock 17 to the correct position and flushing the injected material from the tubing into the patient.

In the operation of valve 10, the inlet 30 is connected to a fluid source 12 via tubing 14 as shown in FIG. 1. Outlet 32 is connected to transducer 16 via tubing 14 which is in turn connected by tubing 14 to the stopcock 17 as shown in FIG. 1 and thence to the catheter 18 which is inserted into the patient's arm. Prior to insertion, the actuator 44 is activated to provide a flush flow, described below, to push the air from the tubing 14 and to fill the tubing with saline solution. Once the catheter 18 is inserted and actuator 44 released, fluid from the source 12 enters into inlet 30 and is blocked in the longitudinal bore 28 by the valve core 40 (FIG. 3). The pressure difference between the fluid source and the patient pushes fluid at a drip rate through the capillary 42 extending through the valve core 40 to the outlet 32. This drip rate flow of saline solution is transmitted through the stopcock and catheter to the bloodstream of the patient to keep the blood surrounding the catheter from clotting.

Figure 4:
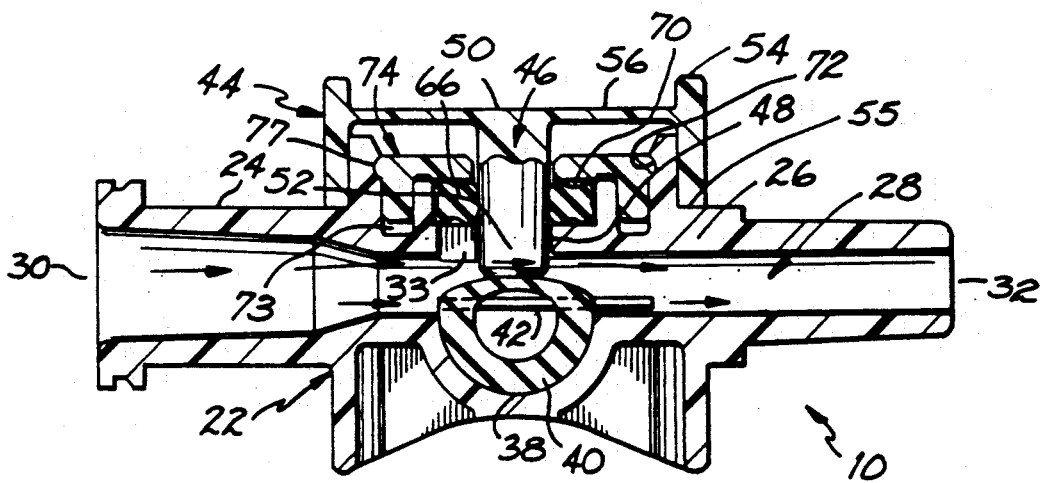
FIG. 4 is a cross-sectional view of the valve as shown in FIG. 3 showing the valve in a fast flush mode.

Flushing the tubing 14 downstream of valve 10 is best shown in FIG. 4. When the upper end 50 of actuating member 46 is pushed downwardly, the lower end 52 of actuating member 46 is urged against the valve core 40 to deform the valve core. Fluid from the inlet 30 of the valve 10 flows through bore 28 by going around actuator member 46 and over the upper surface of the deformed valve core 40 to the outlet 32. This flow is larger in volume than the flow through capillary 42 and is sufficient to flush the tubing and catheter downstream of the valve 10. This flow continues as long as actuator member 46 is held in the position shown in FIG. 4.

Upon release, the radial flange 56 returns to the position shown in FIG. 3 which causes the actuator member 46 to withdraw within the vertical bore 48 so lower end 52 is proximate the valve core 40. The valve core 40 also returns to the shape depicted in FIG. 3 to block bore 2 and terminate the flush flow. The drip flow continues through capillary 42.

One advantage of the valve 10 discussed with respect to the previous FIGS. is its simplicity in manufacturing. As can be seen from FIG. 5, the valve core 40 is press fitted into the valve core bore 38 in valve body 22 to create a fluid tight seal around the valve core in longitudinal bore 28. Capillary 42 is inserted through the open end of a hypodermic type needle and housed within the needle. The needle is inserted through the valve core 40 fitted in bore 38 that is blocking longitudinal bore 28 until the needle point extends through the valve core. Capillary 42 is pushed through the needle until it extends past the needle point and the needle is withdrawn from the valve core to permit the valve core 40 to close about the capillary 42.

O-ring seal 66 is dropped within cavity 70 and cap 74 is snap fitted into groove 72. The lower end 52 of actuator member 46 is inserted through actuator member bore 48 until collar 54 comes to rest on ridge 55. Wings 58 are pivoted about joint 60 to engage plugs 62 in the open ends of the valve core 40 and secure actuator 44 to valve body 22. Wings 58 are pushed until hooks 61 engage grooves 63 to hold the plugs 62 within the core 40. These few simple steps efficiently produce a valve for providing both drip rate and flush rate flows in a catheter system while providing reliable valve operation with a fluid tight seal.

Of course, various changes and modifications of the illustrative embodiment described above will be apparent to those skilled in the art. Such changes and modifications can be made without departing from the spirit and the scope of the invention and without diminishing its attendant advantages. It is therefore intended that such changes and modifications be covered by the following claims.

What is claimed is:

1. A catheter fast flush valve comprising:
    a valve body having a longitudinal bore therethrough for fluid flow through said valve body and a valve core bore substantially transverse to said longitudinal bore and intersecting said longitudinal bore;
    a tube forming an elastomeric valve core inserted in said valve core bore, said tube normally blocking said longitudinal bore through said valve body;
    a capillary longitudinally oriented in said longitudinal bore and extending transversely through said tube, said capillary providing a drip flow path through said tube; and
    means for deforming said tube whereby fluid may flow around said tube through said longitudinal bore.

2. The valve of claim 1 wherein said body has a vertical bore perpendicular to said longitudinal bore and said deforming means further comprising:
    an actuating member slidingly received within said vertical bore perpendicular to said longitudinal bore in said valve body, said actuating member being slidable within said vertical bore to project into said longitudinal bore to deform said tube to unblock said longitudinal bore for flush flow.

3. The valve of claim 2, said deforming means further comprising:
    resilient biasing means mounted about said actuating member to return said actuating member within said vertical bore to a position that permits said tube to substantially block said longitudinal bore.

4. The valve of claim 3, said resilient biasing means further comprising:
    a resilient radial diaphragm connected to said actuating member; and
    a collar mounted about said actuating member and connected to said valve body, said radial diaphragm extending from said actuating member to said collar.

5. The valve of claim 4, said collar further comprising:
    a pair of wings pivotably mounted to said collar, each of said wings having an outboard end adapted to engage said valve body to secure said deforming means to said valve body and to hold said tube within said valve core bore.

6. The valve of claim 5, said valve further comprising:
    said tube extending through said valve core bore to expose open ends in said tube; and
    a plug extending from said outboard end of said wing, said plug being received within said open ends of said tube to expand said tube within said valve core bore whereby the blocking of said longitudinal bore by said tube is improved.

7. The valve of claim 1, said longitudinal bore further comprising:
    an inlet to permit fluid to enter said longitudinal bore;
    an outlet to permit fluid to exit said longitudinal bore; and
    a relief area located in said longitudinal bore adjacent said tube and between said inlet and said tube whereby said relief area permits a back flow to overcome the blocking of said longitudinal bore by said tube and flow over said tube into said longitudinal bore towards said inlet.

8. A method for manufacturing a flush rate flow valve comprising:
    molding a valve body having a longitudinal bore, a valve core bore, and a vertical actuating member bore, said longitudinal bore, said vertical actuating member bore, and said valve core bore being mutually orthogonal to one another;
    press fitting a valve core within said valve core bore to substantially block said longitudinal bore;
    inserting a capillary into said valve core to provide a drip flow path through said valve core and said longitudinal bore;
    inserting a first end of an actuating member into said vertical actuating member bore; and
    resiliently connecting a second end of said actuating member to the exterior of said valve body.

9. The method of claim 8 further comprising:
    mounting a seal about said actuating member; and
    securing said seal about said actuating member.

10. The method of claim 8 further comprising:
    pivoting wings connected to said second end of said actuating member towards said valve body; and
    inserting plugs mounted to said wings into open ends of said valve core exposed within said valve core bore so that said plugs are received in said valve core within said valve core bore to secure said actuating member to said valve body.

* * * * *